United States Patent
Pesso

(10) Patent No.: US 8,366,688 B2
(45) Date of Patent: Feb. 5, 2013

(54) NON-DISCOLORING STERILIZED WIPE

(75) Inventor: Josef Pesso, Holon (IL)

(73) Assignee: Fischer Pharmaceuticals Ltd., Bnei Brak (IL)

(*) Notice: Subject to any disclaimer, the term of this patent is extended or adjusted under 35 U.S.C. 154(b) by 958 days.

(21) Appl. No.: 11/476,445

(22) Filed: Jun. 28, 2006

(65) Prior Publication Data

US 2007/0003605 A1 Jan. 4, 2007

(30) Foreign Application Priority Data

Jul. 4, 2005 (IL) .......................................... 169525

(51) Int. Cl.
- A61M 35/00 (2006.01)
- A61F 13/15 (2006.01)
- A61F 13/40 (2006.01)
- A61F 13/00 (2006.01)
- A61K 8/02 (2006.01)
- A61K 9/70 (2006.01)
- A61L 15/00 (2006.01)
- A61L 15/16 (2006.01)

(52) U.S. Cl. ................. 604/289; 604/1; 604/2; 604/290; 604/294; 604/304; 424/401; 424/443; 424/445; 424/446; 424/447

(58) Field of Classification Search ................. 604/1, 2, 604/289, 290, 294, 304; 206/570, 581, 229, 206/361, 363; 424/401, 427, 429, 443, 764; 510/112, 130, 159

See application file for complete search history.

(56) References Cited

U.S. PATENT DOCUMENTS

| | | | |
|---|---|---|---|
| 3,256,110 A | 6/1966 | Crowe et al. | |
| 3,396,419 A | 8/1968 | Richter et al. | |
| 3,885,047 A * | 5/1975 | Seidehamel et al. | 514/653 |
| 4,215,693 A * | 8/1980 | Rothman et al. | 604/368 |
| 4,533,399 A * | 8/1985 | Mencke | 134/6 |
| 5,384,125 A * | 1/1995 | DiPippo et al. | 424/443 |
| 5,518,146 A | 5/1996 | Mattei | |
| 5,529,784 A * | 6/1996 | DiPippo et al. | 424/443 |
| 5,720,961 A * | 2/1998 | Fowler et al. | 424/401 |
| 5,891,470 A * | 4/1999 | Rinaldi et al. | 424/451 |
| 5,997,887 A * | 12/1999 | Ha et al. | 424/401 |
| 6,153,208 A * | 11/2000 | McAtee et al. | 424/402 |
| 6,190,678 B1 * | 2/2001 | Hasenoehrl et al. | 424/401 |
| 6,206,863 B1 | 3/2001 | Skewes et al. | |
| 6,224,888 B1 * | 5/2001 | Vatter et al. | 424/401 |
| 6,338,855 B1 | 1/2002 | Albacarys et al. | |
| 6,348,508 B1 * | 2/2002 | Denick et al. | 514/772.4 |
| 6,358,516 B1 * | 3/2002 | Harod | 424/401 |
| 6,525,014 B1 * | 2/2003 | Gorlin et al. | 510/439 |
| 6,720,301 B2 * | 4/2004 | Gorlin et al. | 510/439 |
| 6,780,825 B2 * | 8/2004 | Piterski et al. | 510/124 |
| 6,902,743 B1 * | 6/2005 | Setterstrom et al. | 424/489 |
| 7,345,014 B2 * | 3/2008 | Keenan et al. | 510/141 |
| 2002/0086039 A1 * | 7/2002 | Lee et al. | 424/401 |
| 2002/0102289 A1 * | 8/2002 | Drucks et al. | 424/443 |
| 2005/0220742 A1 * | 10/2005 | Breen | 424/70.1 |
| 2005/0244349 A1 * | 11/2005 | Chaudhuri et al. | 424/59 |

FOREIGN PATENT DOCUMENTS

| | | |
|---|---|---|
| WO | WO 98/31403 | 7/1998 |
| WO | WO 01/47357 | 7/2001 |

OTHER PUBLICATIONS

Online encyclopedia article "Chamomile" accessed Jan. 8, 2009. http://en.wikipedia.org/wiki/Chamomile.*
Online encyclopedia article "Viscose" accessed Monday, Oct. 5, 2009. http://en.wikipedia.org/wiki/Viscose.*
Dean D. Metcalfe, Hugh A. Sampson, Ronald A. Simon. Food Allergy: Adverse Reactions to Food and Food Additives. "Chapter 28: Adverse Reactions to Benzoates and Parabens." pp. 369-376. ISBN 0632046015, 9780632046010. John Wiley & Sons, 2003.*
Anonymous: "Roempp Online-Sterilisation" Oct. 31, 2005, XP002398884, retrieved from Internet on Sep. 14, 2006, http://www.roempp.com/prod/index1.html, (3 pages).
ISR in PCT/IL2006/000731 which is the corresponding file of the above US file, (7 pages).

* cited by examiner

*Primary Examiner* — Leslie Deak
*Assistant Examiner* — Adam Marcetich
(74) *Attorney, Agent, or Firm* — Roach Brown McCarthy & Gruber, P.C.; Kevin D. McCarthy

(57) ABSTRACT

A sterilized non-discolored eyelid cleansing pad, which has been sterilized by exposure to γ-radiation in a dose level of 2 Mrad.

7 Claims, No Drawings

NON-DISCOLORING STERILIZED WIPE

FIELD OF THE INVENTION

The present invention relates to the field of personal hygiene. More particularly, the present invention relates to treatment of eyelid inflammation, and maintenance of eyelid hygiene.

BACKGROUND

Eyelid inflammation and associated symptom complex of irritation and crusting of the broad eyelid margin, which includes the eyelashes and associated apocrine and sebaceous glands, are medically diagnosed as blepharitis. This inflammation is frustrating for the patient, particularly the contact lens wearer, and is difficult for the physician to manage. Untreated blepharitis can cause long term structural damages, alongside continuous ocular inflammation and discomfort, and is a major reason for contact lens failure.

Marginal blepharitis can be divided to anterior and posterior types. Anterior marginal blephritis is either an infectious or noninfectious inflammation of anterior eyelid margin that can lead to ocular surface disease. Posterior marginal blepharitis (posterior to the grey line of the lid) is a condition of the eyelid margin characterized by meibomian gland dysfunction that also can be inflammatory and/or infectious. Both kinds are associated with staphylococci infection, and may further be sub-classified based on groupings of observable signs.

Chronic blepharitis is typically connected with crusting and scaling of the eyelid margin, often associated with angular blepharitis at the lateral canthus. Secondary conjunctivitis and marginal corneal infiltrates may be related to direct effects from bacterial exotoxins or to immunologic interactions with staphylococci cell wall antigens. Clinical features include brittle crusting scales on anterior eyelid margin that surround cilia, forming characteristic collarettes. The eyelid margins can be dry, thickened and hyperemic, and the eyelashes tend to mat together in tufts. Chronic inflammation can lead to eyelash loss, whitening, and trichiasis. Structural alterations of the eyelid margin include telangiectasia, hypertrophy, and notching or irregularity.

Controlling the symptoms of chronic blepharitis is possible through eyelid hygiene or cleaning, including use of warm compresses, expressing meibomian gland secretions, and cleaning the eyelid margins to remove keratinized cells and debris. The cleaning process is enhanced by the use of various soaps, particularly those without excessive perfume or lotion content, diluted baby shampoo, and/or commercial lid scrubs, all widely prescribed by ophthalmologists.

Commercially available lid scrubs are widely used for routine eyelid cleansing, and offer a comfortable easy and ready to use treatment, for patients suffering from the symptoms of blepharitis. Lid scrubs are actually disposable pads, which are pre-moistened with an eyelid cleansing composition, and prove to be very useful in the constant maintenance of eyelid hygiene, and in suppressing inflammation of that area.

Keeping the pad sterilized up until use is one basic feature, which is necessary for such eye-care pads. Obtaining pads with such quality requires the exposure to γ-radiation, which proves to be efficient in the final elimination of bacteria from the pad, together with the cleansing composition that they contain.

Although a higher degree of sterilization is desirable in eyelid cleansing pads, it is unfortunately accompanied with the downside of an unpleasant, repelling, anti-hygienically associated discoloration, particularly yellowing, of the pads. Additionally, discolored pads also provide a background, which makes it difficult to distinguish the contamination adsorbed on them during action of cleansing. Overcoming the discomfort imparted to the user with such unpleasant appearance of a hygiene-related product, intended for removal of contamination, is one of the main goals of the present invention, as will be explained hereinafter.

It has surprisingly been found by the inventors of the present invention that a specific concentration range of the ingredients of the pad cleansing composition successfully keeps a pure white appearance of the pad, even when passed through a sterilization process involving exposure to γ-radiation (gamma-radiation). The novel pads using the composition of the invention enjoy both provide a high sterilization standard and an agreeable appearance. It should further be noted that, contrary to many commercially available products intended for the same purpose, the cleansing composition of the invention does not include any preservatives. However, at the same time, it is effective in hygiene maintenance of the eyelid and its surroundings, and benefits in avoiding burning sensations, sensitization of the eye and lacrimation.

It is therefore an object of the present invention to provide a sterilized non-discoloring eyelid cleansing pad.

Still another object of the present invention is to provide a non-discoloring sterilized eyelid cleansing pad.

Still another object of the present invention is to provide a non-discolored sterilized eyelid cleansing pad, which is hypoallergenic and approved according to dermatologic and ophthalmologic requirements.

Still another object of the present invention is to provide a non-discolored highly sterilized eyelid cleansing pad, which does not contain any preservative or preservative-related ingredients, and does not cause irritation, burning sensation to, and lacrimation, and sensitization of the eye upon application to the eyelids.

It is another object of the present invention to provide a non-discolored sterilized eyelid cleansing pad, which is capable of efficiently maintaining the hygiene of the eyelid and eyelid surroundings.

It is yet another object of the present invention to provide a disposable non-discolored sterilized eyelid cleansing pad.

It is a further object of the present invention to provide a non-discolored sterilized eyelid cleansing pad, which is effective for use for all age groups and sexes. Particularly but not limited to, the sterilized pad of the present invention is useful for cleansing gland secretion in infants and children suffering from inflammation, glands secretion, crusting and scaling, for lens wearers, for the removal of make-up for women, and for the elderly who are over-sensitive around the eyes, or in post-surgery conditions.

It is still another object of the present invention to provide a process for preparing a non-discoloring sterilized eyelid cleansing pad, which is effective in hygiene maintenance of the eyelid and eyelid surroundings.

It is a further object of the present invention to provide an eyelid and eyelid surroundings cleansing composition that meets standard regulations of sterilization, for preparing a non-discoloring, essentially purely white cleansing pad for hygiene maintenance of the eyelid and eyelid surroundings in a human subject in need thereof, where the cleansing composition is essentially hypoallergenic, and meets standard ophthalmologic and dermatologic requirements.

This and other objects of the present invention shall become clear as the description proceeds.

SUMMARY OF THE INVENTION

The present invention provides sterilized eyelid cleansing pads, which are passed through a sterilization process involving exposure to γ-radiation in high doses, and are not color affected as a result thereof.

In an effort to provide such a pad, sterilized according to high sterilization standards, yet maintaining a purely white appearance, the inventors have developed specific cleansing compositions, which overcome this problem of the prior art. The inventors have found that when using the concentrations in the composition incorporated in the pad, according to the present invention, the pad does not discolor upon exposure to high doses of γ-radiation during the sterilization process. Thus, passing the pad through a sterilization process as disclosed in the present invention ensures both the practically absolute absence of bacteria in the pad, and therefore the lack of negative undesirable side-effects, which might have been induced otherwise, as well as maintains the original white color of the pad. The final product is, therefore sterilized with a white agreeable appearance.

The cleansing composition incorporated in the sterilized pad of the present invention is detailed in the following Table I. The table shows the range of components according to the invention as well as the most preferred ranges. Most preferred ranges of components are those which combine the best properties of the final product with the non-discoloring properties of the pad. Components' names, general and preferred concentration ranges in weight percent, and specific function in the composition for each are detailed therein.

TABLE I

Components of the Cleansing Composition

| Component name | Range (wt. %) | Most Preferred range (wt. %) | Function |
| --- | --- | --- | --- |
| Water | To-100 | To-100 | water |
| Disodium EDTA | 0.001–3 | 0.01–0.1 | chelating agent |
| PVP (Polyvinyl pyrolidone) | 0.001–5 | 0.001–0.1 | thickener |
| Sodium chloride | 0.001–4 | 0.1–0.9 | stabilizer |
| Sodium phosphate monobasic | 0.001–3 | 0.05–0.5 | pH modifier |
| Sodium phosphate dibasic | 0.001–3 | 0.1–1 | pH modifier |
| Glycerin | 0.001–5 | 0.5–1.5 | moisturizer |
| Polysorbate 20 | 0.001–5 | 0.05–0.2 | surfactant |
| *Camomila Recutita Matricaria* (Chamomile) extract | 0.001–5 | 0.05–0.5 | calmative |
| Lauryl Glucoside | 0.001–5 | 0.1–1 | surfactant |
| pH | 6.5–7.5 | 6.5–7.5 | |

As discussed above, there exists a substantial difference between different processes of sterility of the pad depending upon the level of exposure of the cleansing composition to γ-radiation during the sterilization step. The cleansing compositions of the present invention are exposed to 2 Mrad dose of γ-radiation, and therefore stand the higher requirements of sterilization process. However, as mentioned earlier, such a high dose does not adversely affect the desirable color properties of the pad, where the cleansing composition of the present invention ensures both high sterilization quality and a non-discolored, essentially pure white appearance of the pad. The sterilized pad then comprises a composition which is hypoallergenic, and effective for hygiene maintenance, and inflammation resistance in a human subject when applied to the eyelid, and eyelid surroundings.

GENERAL PRODECURES

In an aspect of the present invention there is provided a process for preparing a cleansing composition, and a pad comprising it. The general outlines of the process of preparation are carried out according to the following description:

Into a main tank is poured all the water content to be used in the preparation of the cleansing composition. PVP is then dissolved in the water, forming an aqueous solution. To the solution formed are next added glycerine, disodium EDTA, sodium chloride, sodium phosphate dibasic, sodium phosphate monobasic, polysorbate 20, and chamomile extract. The mixture is then stirred until total dissolution of the components. As a final step of preparing the solution is added lauryl glucoside, which is then mixed until total dissolution. Quantities employed are within the range disclosed in Table I.

The final solution is screened through an antibacterial filter, and then passed to the filling step. Sachets, containing folded dry pads, are then filled with a pre-determined amount of the cleansing composition prepared in the first stage, and the dry pads thus become pre-moistened. The sachets are then closed by welding, and passed to the final sterilization process.

The closed sachets, containing the pre-moistened pads, are then exposed to γ-radiation in a dose level of 2 Mrad, and the processes of preparation and of sterilization are then complete. The sterilization step is also the final step in the process for preparing the pads, thereby producing pre-moistened pads, having a sterilization level approved by standard regulations, together with a pure white appearance, and containing a cleansing composition, which is eyelid hygiene maintaining, hypoallergenic, and standing ophthalmologic and dermatologic requirements.

In another aspect the present invention provides use of an eyelid and eyelid surroundings cleansing composition that meets standard regulations of sterilization, for preparing a non-discoloring, essentially purely white cleansing pad for hygiene maintenance of eyelid and eyelid surroundings, where the cleansing composition is essentially hypoallergenic, and standing ophthalmologic and dermatologic requirements.

In one embodiment the present invention provides a process for a preparing cleansing composition, and a pad comprising it, where the concentrations ranges of the cleansing ingredients of the cleansing composition are PVP in the range of about 0.001 and about 5 wt. %, glycerine in the range of about 0.5 wt. % and about 1.5 wt. %, EDTA disodium in the range of about 0.01 wt. % and about 0.1 wt. %, sodium chloride in the range of about 0.1 wt. % and about 0.9 wt. %, sodium phosphate monobasic in the range of about 0.05 wt. % and about 0.5 wt. %, sodium phosphate dibasic in the range of about 0.1 wt. % and about 1 wt. %, polysorbate 20 in the range of about 0.05 wt. % and about 0.2 wt. %, chamomile extract in the range of about 0.05 wt. % and about 0.5 wt. %, and lauryl glucoside in the range of about 0.1 wt. % and about 1 wt. %.

In another preferred embodiment the concentrations ranges of the cleansing ingredients in the process provided in the present invention are PVP in the range of about 0.01 and about 1 wt. %, glycerine in the range of about 0.5 wt. % and about 1.5 wt. %, EDTA disodium in the range of about 0.01 wt. % and about 0.1 wt. %, sodium chloride in the range of about 0.1 wt. % and about 0.9 wt. %, sodium phosphate monobasic in the range of about 0.05 wt. % and about 0.5 wt. %, sodium phosphate dibasic in the range of about 0.1 wt. % and about 1 wt. %, polysorbate 20 in the range of about 0.05 wt. % and about 0.2 wt. %, chamomile extract in the range of about 0.05 wt. % and about 0.5 wt. %, and lauryl glucoside.

An illustrative example of a composition according to a preferred embodiment of the present invention is an eyelid, and eyelid surroundings cleansing composition that meets standard regulations of sterilization, essentially containing, in aqueous solution, 0.01 wt. % PVP, 0.1 wt. % of glycerine, 0.05 wt. % of EDTA disodium, 0.3 wt. % of sodium chloride, 0.1 wt. % of sodium phosphate monobasic, 0.67 wt. % of sodium phosphate dibasic, 1 wt. % of polysorbate 20, 0.1 wt. % of chamomile extract, and 0.3 wt. % lauryl glucoside for preparing a non-discoloring, essentially purely white cleansing pad for hygiene maintenance of eyelid and eyelid surroundings, where the cleansing composition is essentially hypoallergenic, and standing ophthalmologic and dermatologic requirements.

The following exemplifies preferred embodiments of the cleansing composition, and the process of preparing a sterilized cleansing pad. Ophthalmologic and dermatologic assays, demonstrating the pad's hygiene maintenance efficiency carried out on patients according to standard regulations, are also provided. It is to be understood, however, that the following examples are illustrative only, and are not presented in order to limit in any way the scope of the present invention, yet without exceeding it.

EXAMPLE 1

Preparation of a Sterilized Cleansing Pad Containing a Cleansing Composition

PVP in concentration of 0.01 wt. % is added into a 300 lt. tank containing water in an amount pre-calculated to complete the weight percent of the final solution composition to 100 wt. %, and dissolved until total dissolution. 0.1 wt. % of glycerine, 0.05 wt. % of EDTA disodium, 0.3 wt. % of sodium chloride, 0.1 wt. % of sodium phosphate monobasic, 0.67 wt. % of sodium phosphate dibasic, 1 wt. % of polysorbate 20, and 0.1 wt. % of chamomile extract are next added to the PVP solution and mixed until total dissolution. Lauryl glucoside 0.3 wt. % is finally added to the tank and mixed until total dissolution.

The solution is then screened through a 0.2 micron antibacterial filter, and passed to a filling machine. In the filling machine, 3 grams of the solution are poured into each sachet, which contains an embossed type folded dry pad made of 65% Viscose and 35% PET (Polyethyleneterephthalate), having a weight/area ratio of 55±5 g/m$^2$, a thickness of 0.80±0.08 mm and an absorption capacity of >8 g/g. The pad then becomes pre-moistened. After filling, the sachets are then welded and passed to a sterilization step by exposure to γ-radiation in a dose level of 2 Mrad per sachet. The sterilization step is also the final step in the process of preparing the pads, thereby producing the pre-moistened pads, having high sterilization level approved by standard regulations, together with a pure white appearance, and containing a cleansing composition, which is eyelid hygiene maintaining, hypoallergenic, and standing ophthalmologic and dermatologic requirements.

One point concerning the pad is that since it is of an embossed type, that is having a textured surface area, then its practical surface area is larger than area calculated based on its spatial dimensions. Furthermore, its cleansing effect is improved, enabling a more efficient collection of residues, or crusting, especially when employed on smooth surfaces.

EXAMPLE 2

Determination of Sensitizing Properties of One Product by Draize Repeated Insult Patch (RIPT) Test in Human Volunteers The above study was carried out in accordance with the Good Clinical Practice and Standards established by the International Standardization Organization (ISO), and the standard operation procedures of the Institute for Skin Research (ISR).

The sensitization properties of the test material of Example 1 were evaluated by a patch preparation consisting of an occlusive application of the product by Finn Chambers (aluminum cells of some 20 microliters) on the volunteers. Each patch contained the test material. The method employed in carrying out the test is similar to that described in "Appraisal of the Safety Chemicals in Foods, Drugs and Cosmetics" by J. H. Draize and published by association of Food and Drug Officials of the United States.

The test involved application of the test article to the back of a group of 50 volunteer panelists. The panelists ranged from 18 to 64 years of age. These panelists were determined to be in good general health and free of any visible skin disease or anomaly in area to be patched. Each panelist was required to read, understand and sign an informed consent statement.

Induction Phase:

The patch was applied to its designated contact site and remained in place for 24 hours. At the end of this period the patch was removed and the site was examined again. A patch was then applied to the same site as previously used. The second application was identical to the first and remained in place for 24 hours. This procedure was repeated on Mondays, Wednesdays, and Fridays, or Sundays, Tuesdays and Thursdays until a series of nine applications were made. The panelists examined the site for any dermal response and reported their observations prior to the next application. The same site was used throughout the study. Each application was put on and removed by the staff of the Institute. A quality control person monitored adherence to study protocol.

Challenge Phase

Following the 9$^{th}$ application: a rest period of 2 weeks elapsed after which a challenge application was applied in the same manner and to the same site described above. The challenge application was removed after 24 hours and the site was examined and graded for signs of irritation or sensitization. A follow-up examination was conducted at 48 hours after the challenge application (24 hours after patch removal), as well as at 48 and 72 hours after removal.

The test results were appreciated according to the following grading scale:

0 No visible reaction
? Doubtful reaction: faint, minimal erythema, no infiltration
1 Weak positive reaction: erythema, infiltration, no discrete papules
2 Strong positive reaction: erythema, infiltration, papules, discrete vesicles
3 Extra positive reaction: intense erythema, infiltration, coalescing vesicles/bullous reaction
IR Irritation reaction: discrete erythema without infiltration/patchy follicular erythema/hemorrhagic and follicular pustules
NT Not tested Table II summarizes the characteristics of the subjects tested in this study.

TABLE II

| | | Subjects characteristics | |
|---|---|---|---|
| Product | Sex | Average Age | Medical history likely to influence study |
| 1 | F | 39.64 | None |
| 1 | M | 38.18 | None |

Results:
1. The original patch sites exhibited no reactions during the Induction Phase, the Rest Period, or the Challenge Phase.
2. No other reactions were exhibited.
3. At the Challenge Phase (the $10^{th}$ application), no reaction was observed in any of the volunteers.

Conclusions:
In this RIPT Study performed according to aforementioned Experimental Design, after repeated applications, the tested material did not induce in the $10^{th}$ application (Challenge Phase) a contact dermal irritation and/or sensitization in human subjects.

EXAMPLE 3

Ophthalmological In-Use Safety Evaluation

The objective of this test was to evaluate the in-use safety of the product of Example 1, following four consecutive weeks of use by a panel of 47 female and male volunteers of whom 24 were contact lens wearers and all of whom were regular users of eye-makeup, ranging in age from 18 to 65 years. Pre and post test eye examinations were performed by an ophthalmologist to support the claims of "Ophthalmology-Tested". Each panelist completed a brief Medical History Form.

In selecting the subjects for this test the following criteria were considered:
1. Female subjects users of eye-makeup, and contact lens wearers were allowed in the test.
2. Also allowed in the test were subjects free of any clinically significant ophthalmic findings such as external ocular diseases or infections of the eyes and/or eyelids, glaucoma, cataracts, corneal opacities, or maculopathies that could have progressed during the course of this study.
3. Disqualified for this test were subjects exhibiting or having a known history of acute or chronic dermatological, medical, and/or physical conditions that could influence the outcome of the test.
4. Also disqualified were subjects having a known history of allergic reactions to cosmetics, soaps, or toiletries; subjects undergoing treatment with sympathomimetics, antihistamines, non-steroidal anti-inflammatory agents, corticosteroids, and/or any other medications that could have interfered with the results of this study, within one week prior to initiation of this test; subjects abusing alcohol, and/or drugs; pregnant and/or lactating women.

Each subject was instructed to use the test products at least once daily in her usual fashion. The subject was instructed to record the dates and times of use on a daily diary. The subjects were instructed to call in if they experienced any discomfort while using the test products, to continue their usual cosmetic regimen, with the exception of new cosmetics during the study period other than the provided eye test materials, and to use only eye products related to routine care of their contact lenses. Mid-point evaluation of the subjects was carried out after two weeks use period. A final ophthalmic examination was conducted after a total of four weeks of product use. On the initial examination, all subjects were tested for baseline visual acuity using a Snellen Eye Chart.

All subjects had subjective ocular irritation, lacrimation, lid cornea, and contact lens scores of zero (0). Subjects who exhibited palpebral and/or bulbar conjunctival irritation scores of level one (1) on the initial visit were allowed to be empanelled. This latitude was to allow inclusion of subjects who normally exhibited a baseline of mild irritation as a result of contact lenses wear, and/or environmental and seasonal factors.

At the end of a two week period, each subject's subjective irritation status was determined. A final ophthalmic examination, including visual acuity, and subjective and objective ophthalmic evaluation, was conducted after the four week use period in a similar fashion.

The symptoms examined in this assay, were evaluated separately, and rating of each took an integer value between 0 and 3, depending on the severity of expression of each symptom. The symptoms measured were subjective irritation (stinging, burning, itching, dryness); lacrimation (ophthalmologist's estimation); bulbar and pulpebral conjunctival irritation (ophthalmologist's evaluation); follicular and/or papillary reaction in the plapebral conjuntiva; follicular and/or papillary reaction in the bulbar conjunctiva; scaling, redness, swelling on the margins of the upper eyelid and the lower lid; and cornea epithelial defects, neovascularization or opacities.

Conclusions:
Under the conditions of this study, the tested material, when used daily for a four week period by a test panel of 47 female and male subjects, including 24 contact lens wearers, did not elicit any evidence of ophthalmic irritation or sensitization. Subject's lacrimation, lids palpebral conjunctival irritation, bulbar conjuntival irritation, and cornea were examined at the initiation of the test period, and at the termination of the test. According to the test results, this product has been found to be safe for usage around the eye area.

While examples of the invention have been described for purposes of illustration, it will be apparent that many modifications, variations and adaptations can be carried out by persons skilled in art, without exceeding the scope of the claims.

The invention claimed is:
1. A disposable, sterilized, hypoallergenic, purely white eyelid cleansing pad consisting of components:
  i) viscose and polyethyleneterephthalate, having a textured surface area; and
  ii) an aqueous cleansing solution, screened through a 0.2 micron antibacterial filter, consisting of
    glycerin in a range from about 0.001 wt. % to about 5 wt. %,
    EDTA disodium in a range from about 0.001 wt. % to about 3 wt. %,
    sodium chloride in a range from about 0.001 wt. % to about 4 wt. %,
    sodium phosphate monobasic in a range from about 0.001 wt. % to about 3 wt. %,
    sodium phosphate dibasic in a range from about 0.001 wt. % to about 3 wt. %,
    polysorbate 20 in a range from about 0.001 wt. % to about 5 wt. %,
    chamomile extract in a range from about 0.001 wt. % to about 5 wt. %,
    lauryl glucoside in a range from about 0.001 wt. % to about 5 wt. %, and
    PVP in a range from about 0.001 wt. % to about 5 wt. %, wherein said components have been sterilized by exposure to γ-radiation in a dose level of 2 Mrad and remained non-discolored, and are essentially free from a preservative.

2. The pad as claimed in claim 1, wherein
the glycerin is in a range from about 0.5 wt. % to about 1.5 wt. %,
the EDTA disodium is in a range from about 0.01 wt. % to about 0.1 wt. %,
the sodium chloride is in a range from about 0.1 wt. % to about 0.9 wt. %,
the sodium phosphate monobasic is in a range from about 0.05 wt. % to about 0.5 wt. %,
the sodium phosphate dibasic is in a range from about 0.1 wt. % to about 1 wt. %,
the polysorbate 20 is in a range from about 0.05 wt. % to about 0.2 wt. %,
the chamomile extract is in a range from about 0.05 wt. % to about 0.5 wt. %,
the lauryl glucoside is in a range from about 0.1 wt. % to about 1 wt. %, and
the PVP is in a range from about 0.001 wt. % to about 0.1 wt. %.

3. The pad as claimed in claim 1, having the sterilization by exposure to γ-radiation in a dose level of 2 Mrad after having been moistened by the aqueous cleansing composition consisting of
about 0.1 wt. % of glycerin,
about 0.05 wt. % of EDTA disodium,
about 0.3 wt. % of sodium chloride,
about 0.1 wt. % of sodium phosphate monobasic,
about 0.67 wt. % of sodium phosphate dibasic,
about 1 wt. % of polysorbate 20,
about 0.1 wt. % of chamomile extract,
about 0.3 wt % lauryl glucoside and
about 0.01 wt. % of PVP.

4. The pad as claimed in claim 1, organized to maintain hygiene of the eyelid and eyelid surroundings in a human subject.

5. The pad as claimed in claim 1, organized to be suitable, according to ophthalmologic requirements, for suppressing subjective irritation (stinging, burning, itching, dryness); lacrimation (ophthalmologist's estimation); bulbar and pulpebral conjunctival irritation (ophthalmologist's evaluation); follicular and/or papillary reaction in the plapebral conjuntiva; follicular and/or papillary reaction in the bulbar conjunctiva; scaling, redness, swelling on the margins of the upper eyelid and the lower lid; and cornea epithelial defects, neovascularization or opacities in a human subject.

6. The pad as claimed in claim 1, wherein said pad is organized to be for use for all age groups and both sexes; for cleansing gland secretion in infants and children suffering from a condition selected from the group consisting of inflammation, glands secretion, crusting, and scaling; for lens wearers;
for women for make-up removal; for the elderly being over-sensitive around the eyes; and/or for subjects with post-surgery conditions.

7. The pad as claimed in claim 1, which is hypoallergenic and organized to be approved according to dermatologic requirements, and wherein said pad does not induce dermal irritation or sensitization.

\* \* \* \* \*